United States Patent [19]
Franetzki et al.

[11] Patent Number: 5,598,454
[45] Date of Patent: Jan. 28, 1997

[54] X-RAY DIAGNOSTICS INSTALLATION

[75] Inventors: Manfred Franetzki; Werner Guenther; Josef Ploetz, all of Bensheim, Germany

[73] Assignee: Siemens Aktiengesellschaft, Munich, Germany

[21] Appl. No.: 420,215

[22] Filed: Apr. 11, 1995

[30] Foreign Application Priority Data

Apr. 26, 1994 [DE] Germany ........................... 44 14 689.2

[51] Int. Cl.⁶ ....................................................... A61B 6/14
[52] U.S. Cl. ................................. 378/206; 378/170
[58] Field of Search ........................... 378/170, 206, 378/168, 177, 178, 208

[56] References Cited

U.S. PATENT DOCUMENTS

| | | | |
|---|---|---|---|
| 2,976,417 | 3/1961 | Freeman | 378/170 X |
| 3,454,763 | 7/1969 | Goldenthal | 378/170 X |
| 3,473,026 | 10/1969 | Updegrave | 378/170 |
| 4,598,416 | 7/1986 | Donato | 378/170 X |

FOREIGN PATENT DOCUMENTS

WO93/22893  11/1993  WIPO.

OTHER PUBLICATIONS

"Simplified and Standardized Bisecting–Angle Technic for Dental Radiography," Updegrave, Journal of the American Dental Association, vol. 75 (1967), pp. 1361–1368.

Siemens Publication "Bildgebende Systeme für die Medizinische Diagnostik," pp. 380–381 No date.

Primary Examiner—David P. Porta
Attorney, Agent, or Firm—Hill, Steadman & Simpson

[57] ABSTRACT

An x-ray diagnostics installation includes a device for positioning a radiation emitter such that the reference ray of an emitted ray beam always and automatically intersects a reference axis that is stationary with reference to said device at an acute angle α when the radiation emitter is coupled to the device. X-ray exposures for tomosynthesis can thus be produced in a simple way.

18 Claims, 3 Drawing Sheets

X-RAY DIAGNOSTICS INSTALLATION

BACKGROUND OF THE INVENTION

1. Field of the Invention

The present invention is directed to an x-ray diagnostics installation of the type for producing medical x-ray images, such as dental x-ray images.

2. Description of the Prior Art

A conventional x-ray installation has a radiation emitter that is adjustably held at a wall of a room or at a stand. In order to produce an x-ray exposure, the radiation emitter is aligned with reference to an examination subject and an x-rays are generated which penetrate the examination subject and are then incident on a radiation receiver. The radiation receiver can be implemented as x-ray film, an image intensifier video chain or a CCD radiation converter.

In a known way, such a radiation receiver converts the x-ray shadow proceeding from the examination subject into state changes in the case of film, or signals in the case of electronic detection, so that a two-dimensional image is obtained, or can be calculated on the basis of the signals. The x-ray shadow arises from the absorption sum of all penetrated layers of the subject. The spatial allocation of the image content of the two-dimensional image is made by the viewer on the basis of his or her experience. When, however, diagnostically relevant details are occluded by more highly absorbent structures or when pseudo-structures arise, then these can remain hidden from even the most experienced viewer or can lead to misdiagnoses. This is true, of course, because of the complex bone structures, especially when producing x-ray exposures in the tooth or jaw region in dental diagnostics.

An improvement in the ability to diagnose the contents of images of a subject to be examined is achieved on the basis of a three-dimensional or a slice-by-slice image presentation. Such three-dimensional or slice-by-slice presentations can be obtained, for example, by computed tomography or nuclear magnetic resonance tomography. The technical outlay and thus the costs, however, are thereby substantial.

Tomosynthesis comes into consideration as an alternative. In tomosynthesis, an examination subject is irradiated from different projection directions and the x-ray shadow is imaged on a radiation receiver. Particularly in the case of radiation receivers which generate electrical signals dependent on incident x-ray shadows, tomograms or three-dimensional images can be calculated with known methods. The number of necessary exposures and the solid angle of the fluoroscopy are set dependent on the desired depth resolution of the slice thickness of an image.

In conventional tomograms (tomography), a radiation emitter and a radiation receiver are coupled and adjusted oppositely relative to one another. Subjects that lie in the focal plane are sharply imaged since they are always projected onto the same location of the radiation receiver during the opposed adjustment. Subjects that lie outside the focal plane are imaged unsharp since they are projected onto different locations of the radiation receiver during the opposed adjustment. For producing an interpretable exposure, the subject in the focal plane is imaged onto the radiation receiver with a number of individual projections at projection angles $\alpha$. By direct superimposition of the radiation images acquired by the individual projections, a tomographic image of the subject in the focal plane can be produced. A tomographic image of a subject that is arranged in a plane parallel to the focal plane can be produced by shifting the radiation images acquired by the individual projections by distances $\Delta S$ relative to one another before the superimposition. The size and the direction of the shift $\Delta S$ is dependent on the position of the radiation emitter and on the location (attitude) of the plane to be reconstructed.

The shift $\Delta S$ for what is referred to as linear tomography, wherein the radiation emitter is adjusted in one dimension, is determined from the equation Bildgebende Systeme für die medizinische Diagnostik, Krestel, (Siemens) pages 380 and 381)

$$\Delta S\,H = \frac{x \cdot h}{x - y - h} \cdot \tan \alpha$$

wherein:

x=distance of the focus of the radiation emitter from the radiation receiver, h=distance of the focal plane from the plane in which a subject is to be reconstructed, y=distance of the focal plane from the plane of the radiation receiver, and $\alpha$=projection angle, i.e. the angle that a reference beam of the ray beam assumes relative to a reference axis, whereby the reference axis is aligned perpendicularly relative to the focal plane.

When the radiation receiver converts the received x-ray shadow of the subject into electrical signals, digital tomosynthesis enables the reconstruction of tomographic images in a number of planes from the signals of the individual projections of the subject that were produced given different projection angles: Known, digital image generating and processing systems can be employed in digital tomosynthesis for producing a visible image from the signals of the radiation receiver.

PCT Application WO 93 22 893 discloses a method with which it is possible to reconstruct an exposure of a subject without the projection angles $\alpha$ and the geometrical arrangement of radiation emitter, radiation receiver and focal plane being known. According to this method, a reference of radiation-absorbent material having a known size and known distance from the radiation receiver is provided in the region of the radiation receiver, this reference being projected onto the radiation receiver in every individual projection. The geometrical arrangement and the two-dimensional projection angle $\alpha$ can be identified on the basis of the spatial imaging of the reference on the radiation receiver for each individual projection. This reconstruction is time-intensive and complex due to the extensive calculations.

The radiation emitter must assume predetermined positions and alignments relative to the examination subject for obtaining an image sequence that can be interpreted tomosynthetically. The alignment can be set, for example, by an operator of the x-ray diagnostics installation or by employing and driving a radiation emitter that has multiple foci. Manual alignment requires several operating steps and is thus time-consuming and susceptible to error. The employment of a radiation emitter having multiple foci is technologically complicated, and thus expensive.

SUMMARY OF THE INVENTION

An object of the present invention is to implement an x-ray diagnostics installation of the type initially described which can produce x-ray images for tomosynthesis in a simple way. Another object is to provide an x-ray diagnostics installation fashioned for that purpose which is less technologically complicated than known systems but nonetheless is reliable in employment.

These objects are inventively achieved in an x-ray diagnostics installation having a device for positioning a radiation emitter so as to always and automatically cause a reference ray of an x-ray beam emitted by the radiation emitter to intersect a reference axis that is stationary with respect to the device at an acute angle α when the radiation emitter is coupled to the device. An advantage of the invention is that the angle between the reference ray and the reference axis, and thus the projection angle α, is predetermined, so that a calculation of an x-ray image from the signals of the radiation converter is possible in a simple way.

The description of the positioning device as "always and automatically" causing the reference ray to intersect the reference axis at an acute angle α does not preclude the possibility of the device being adjustable so as to permit the acute angle α to be change from examination-to-examination. For a series of exposures for producing a tomographic image, however, the angle α, once set, will not vary from projection-to-projection, and the positioning device of the invention permits the radiation emitter to automatically and always be positioned so as to produce the same acute angle for each exposure position.

In an embodiment, the device includes a disk having a recess for the acceptance of a part of the radiation emitter, particularly for the tube or barrel of the radiation emitter, and a drive for the disk, the latter being adjustable around its longitudinal axis. For producing a series of x-ray exposures for tomosynthesis, the radiation emitter merely has to have its tube or barrel introduced into the recess, as a result of which the angle of the reference ray relative to the reference axis is automatically prescribed. The direction of the irradiation is prescribed positionally dependent by triggering x-rays at predetermined positions during an adjustment of the disk. A better mixing of subject details lying outside the reconstructed plane is achieved if the adjustment of the radiation emitter takes place in two dimensions, for example on a circular orbit; the size and direction of the shift ΔS then also arise analogously to the aforementioned equation.

In another embodiment of the invention, the device is annularly fashioned and has at least two recesses for the acceptance of the radiation emitter, preferably the tube or barrel of the radiation emitter. Given a predetermined angle, the reference ray intersects the reference axis in a first predetermined direction when the radiation emitter is accepted in the first recess and intersects it in a second predetermined direction when the radiation emitter is accepted in the second recess. The irradiation direction and the angle α of the reference ray relative to the reference axis are predetermined and defined by the recesses, particularly by aligning their respective central longitudinal axes. The recesses are thereby preferably implemented as circular segments, so that the tube or barrel can be placed against them.

DESCRIPTION OF THE PREFERRED EMBODIMENTS

Figure 1:
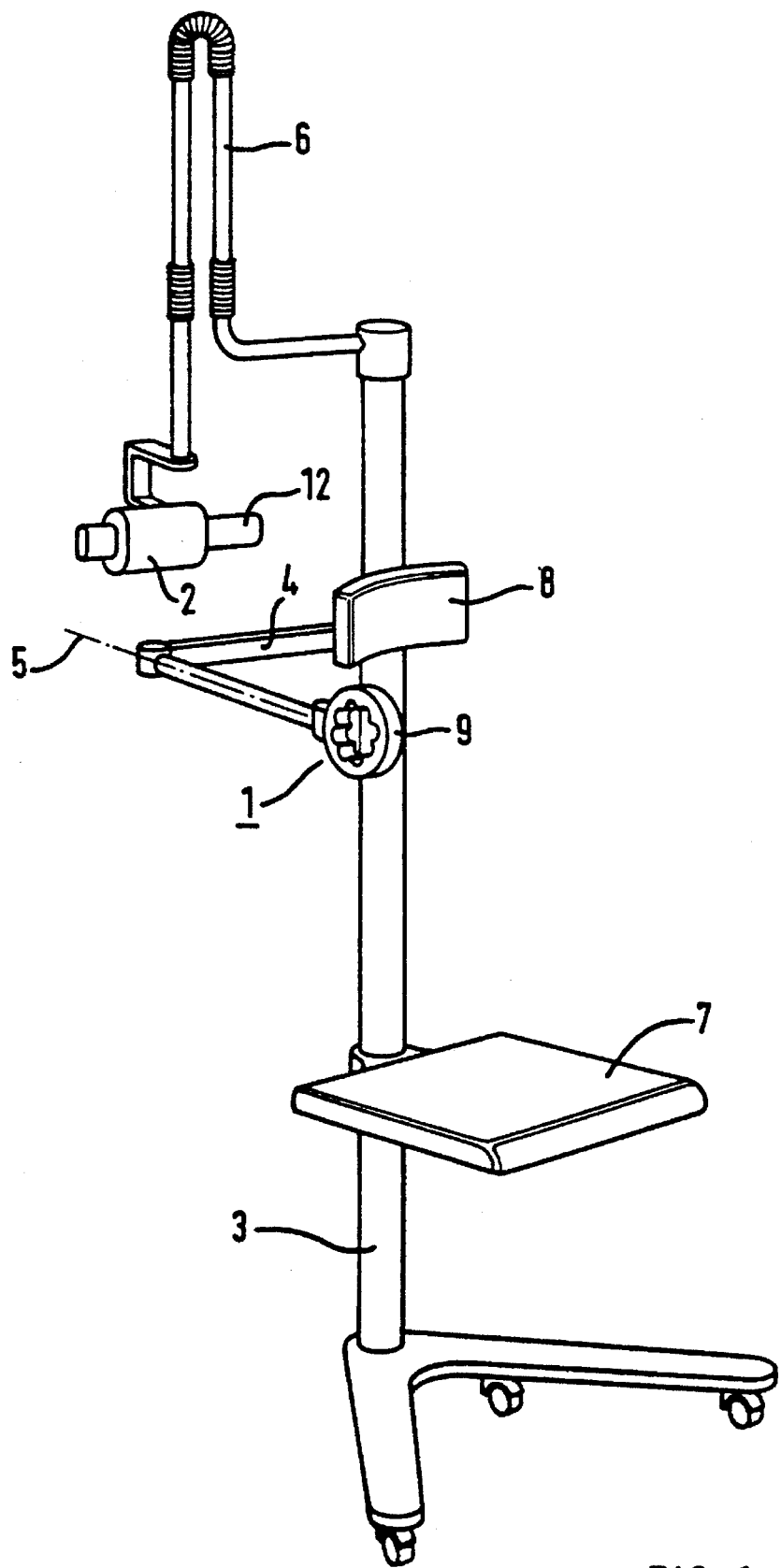
FIG. 1 shows a first embodiment of an x-ray diagnostics installation of the invention.

FIG. 1 shows a dental x-ray diagnostics installation that includes a device 1 for positioning a radiation emitter 2 that is seated at an adjustable column 3. The device 1 is adjustable along the column 3 via an articulated arm 4, is pivotable around the longitudinal axis of the column and is seated so as to be rotatable around an axis 5 of the articulated arm 4.

The radiation emitter 2 is adjustably held at the column 3 via a retainer arm 6, so that it can be positioned with reference to an exposure subject for producing an x-ray exposure.

A seat 7 for an examination subject is mounted on the column 3 so as to be adjustable along the column 3 and pivotable around the longitudinal axis thereof. A head support 8 is likewise adjustably mounted on the column 3.

For producing an intraoral x-ray exposure for tomosynthesis, it is necessary to irradiate an exposure subject, for example a tooth, from different directions. A radiation receiver converts the X-radiation incident from the different directions into signals that are supplied to an evaluation unit for producing an x-ray image of the exposure subject. Knowledge of the angle α of the reference ray of a ray beam emitted from the radiation emitter 2 relative to a reference axis is required for the calculation of such an x-ray image. According to the invention, the dental x-ray diagnostics installation therefore employs the device 1 for positioning the radiation emitter 2 such that the reference ray of an emitted ray beam always and automatically intersects a reference axis of the device 1 at an acute angle in a reference point when the radiation emitter 2 is coupled to the device 1.

Figure 2:
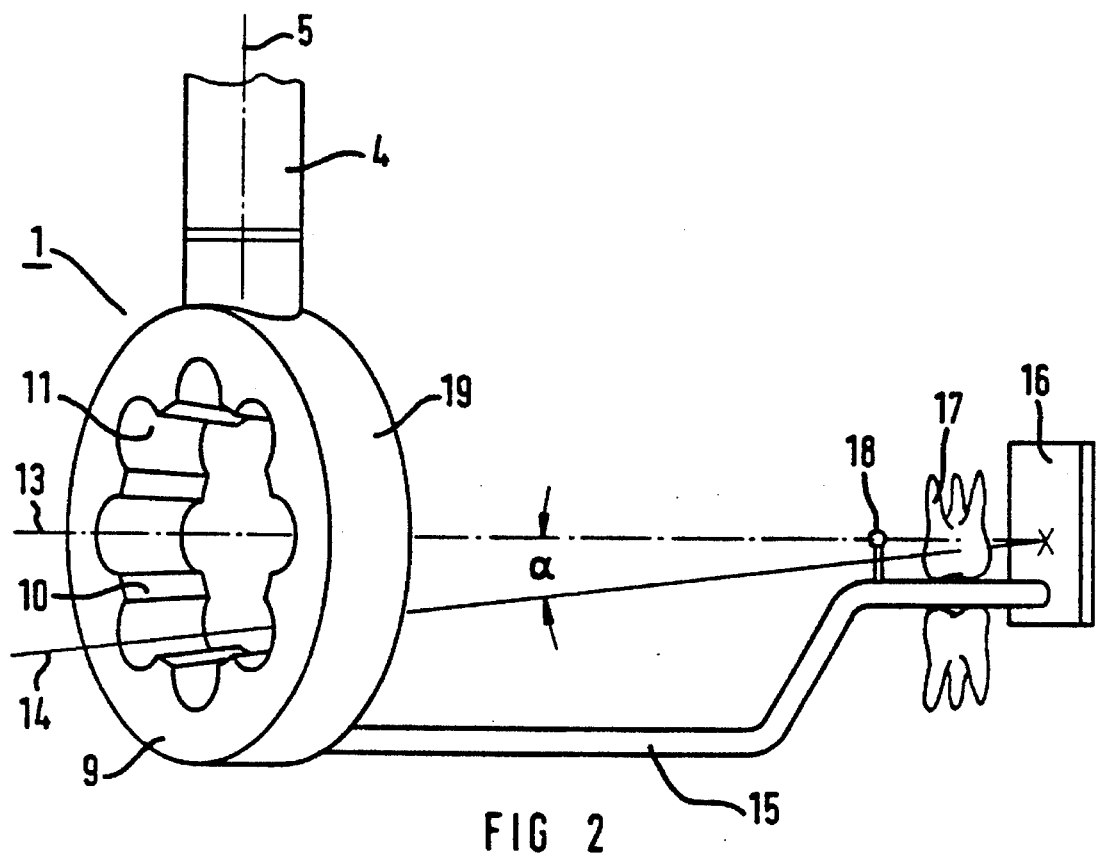
FIG. 2 shows the positioning device in the first embodiment of FIG. 1 in more detail.

The device 1 of FIG. 1 is shown in detail in FIG. 2. The device 1 has a disk 9 in the form of a ring having an inside edge 10 provided with a number of recesses 11. These recesses 11 serve the purpose of coupling the radiation emitter 2, particularly the tube or barrel 12 thereof, to the device 1. As a result of the recesses 11 that, for example, extend along a circular arc whose center lies on a reference axis 13 of the device 1, a number of positions of the radiation emitter 2 and—due to the alignment of the central longitudinal axis thereof—a number of irradiation directions are automatically prescribed. The angle α at which a reference ray, for example the central ray of an x-ray beam emitted by the radiation emitter 2, intersects the reference axis 13 of the device 1 in a reference point is thus always predetermined by inserting the tube or barrel 12 into a recess 11. According to the invention, the device 1 has at least two and preferably eight recesses 11 formed as circular segments for the positioning of the radiation emitter 2. It has proven advantageous for the calculation of an x-ray image and in order to produce a device 1 when the angle α lies in the range below 45°, preferably below 15°.

In the exemplary embodiment, a bracket 15 for a radiation converter 16 that prescribes the distance of a schematically indicated tooth 17 from the device 1, and thus from the focus of the radiation emitter 2, can be coupled to the device 1. The distance is preferably selected such that the reference ray 14 of the x-ray beam is incident at the center of the radiation converter 16. When the radiation converter 16 is arranged in the focal plane and at the reference point, then a calculation of an image from the signals of the radiation converter 16 is possible in a desired plane in a simple way. The shift ΔS is then directly dependent on the distance between the reconstructed plane and the focal plane (distance from the radiation converter 16), and a constant factor.

In order to avoid exposures from being made when the radiation emitter 2 is not exactly accepted by the device 1, so that the angle α is different and/or the distance between the focus of the radiation emitter 2 and the radiation receiver 16 is not exactly observed, or if these particulars are not known or are not known with the required precision, it is advantageous to provide a reference 18 of radiation-absorbent material and which, for example, is spherically fashioned. The reference 18 is held in front of the tooth 17 and the radiation converter 16 as seen in the radiation propagation direction. As a consequence of the projection of the reference 18 onto the radiation receiver 16 (which is dependent on the projection angle a and on the distance between the focus of the radiation emitter 2 and the radiation receiver 16) and as a consequence of the signals thereby generated, a subsequent calculation of the protection angle α and of the distance is possible. Given employment of such a reference 18, the bracket 15 can be composed of elastic material, so that it allows the patient whose tooth is to be examined a limited freedom of movement.

It is also within the context of the invention, to provide the recesses 11 at the outside edge 19 of the disk 9, for example as circular segments. Further, the distance of the device 1, or of the radiation emitter 2 from the exposure subject can be prescribed or acquired in a non-contacting, wireless manner (for example, with optical or acoustic means).

Figure 3:
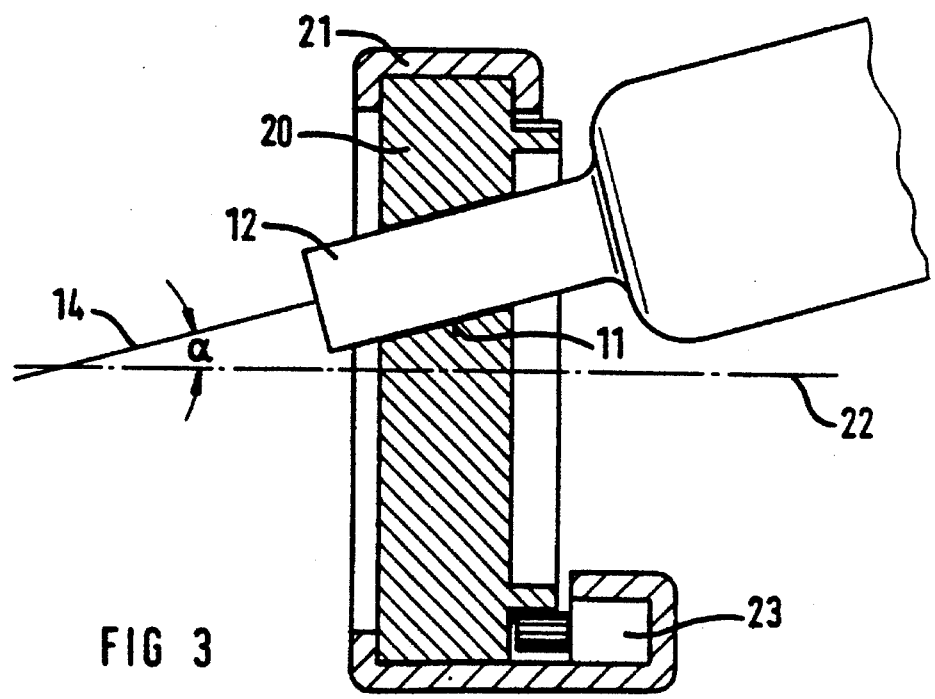
FIG. 3 is a side view, partly in section, of a second embodiment of a positioning device constructed in accordance with the principles of the present invention.

In the further exemplary embodiment of the device 1 shown in FIG. 3, a circular disk 20 is mounted in a housing 21 so as to be rotatable around its central axis 22. It is possible to manually rotatably adjust the circular disk 20; however, it is advantageous to provide a drive 23 therefor that engages the circular disk 20, such as by meshing. The circular disk 20 has a recess 11 for coupling the radiation emitter 2, preferably the tube or barrel 12 thereof. The annular position of the recess 11 is adjusted by operating the drive 23 so as to move the recess 11 along a circular arc whose center lies on the reference axis. The alignment of the central longitudinal axis of the recess 11 thereby also automatically prescribes the projection angle α that the reference ray 14 assumes relative to the reference axis, namely the central axis 22. When the radiation emitter 2 is coupled thereto, an adjustment of the circular disk 20 around its central axis 22 changes the direction of the irradiation. The drive of the radiation emitter 2 for emitting a ray beam can ensue automatically when the circular disk 2, especially the recess 11 thereof, assumes predetermined positions.

Figure 4:
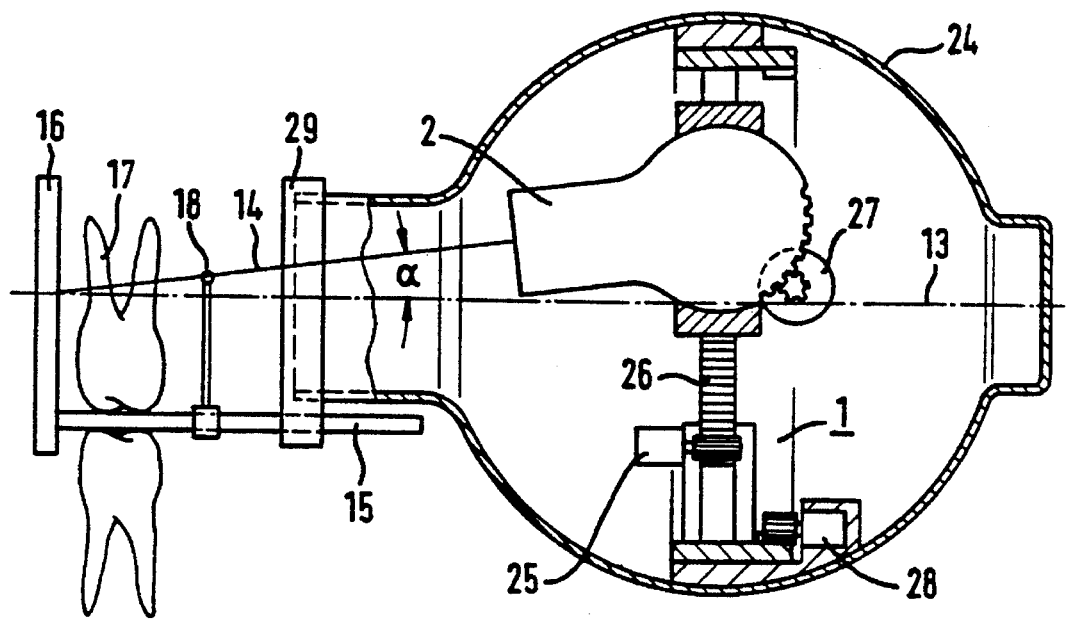
FIG. 4 is a side view, partly in section, of a third embodiment of a positioning device constructed in accordance with the principles of the present invention.

In the exemplary embodiment shown in FIG. 4, the radiation emitter 2 and the device 4 are arranged in a common housing. The device 1 for positioning the radiation emitter 2 is implemented such that the radiation emitter 2 is adjustable at guides in a direction perpendicular to the reference axis 11. This adjustment takes place by means of a toothed rack 26 that is rotatable via a first drive 25. A second drive 27 is provided for swivelling of the radiation emitter 2, so that the reference ray 14 either describes an acute angle α with the reference axis 13 or can be aligned parallel thereto. A third drive 28 engages the device 1 for the adjustment thereof around the reference axis 13. As a result of the compact unit composed of the radiation emitter 2 and the device 1, exposures of the tooth 17 can be produced from different directions. Swivelling of the radiation emitter 2 is preferably accomplished such that the reference ray 14, given a prescribed distance of the radiation converter 16, is always incident at the center of the converter 16.

A gating mechanism 29 for the x-ray beam as well as the bracket 15, can be mounted on the housing 24.

Figure 5:
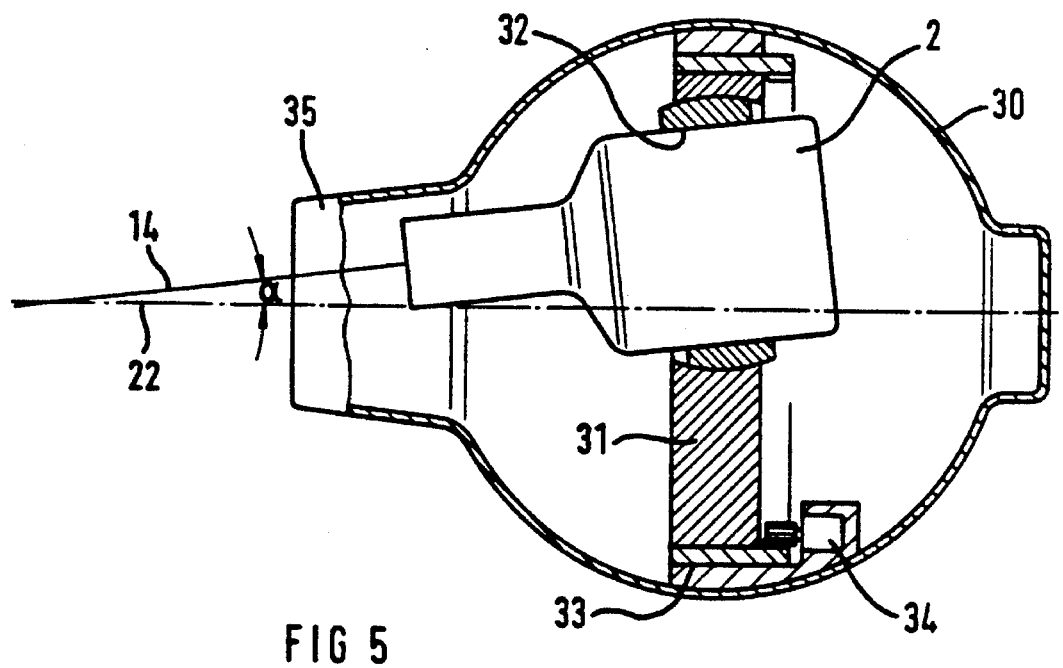
FIG. 5 is a side view, partly in section, of a fourth embodiment of a positioning device constructed in accordance with the principles of the present invention.

According to another exemplary embodiment of the invention shown in FIG. 5, the radiation emitter 2 is held by a wobble bearing in a housing 30. The wobble bearing has a swash plate 31 which holds a sliding, frictional bearing 36 in which a recess 32 accepting the radiation emitter 2 is provided. Bearings 33 engage the edge of the swash plate 31, so that the swash plate 31 is rotatable around the reference axis 22. A drive 34 is provided that engages the swash plate 31 for rotation thereof. A tube or barrel 35 is provided at the housing 30 so that the radiation emitter 2 can rotate through the entire solid angle that is prescribed by the recess 32. The angle α that the reference ray 14 assumes relative to the reference axis 22 also lies in a range from 2° through 12°, preferably at 8°. This embodiment also makes it possible to irradiate an examination subject from either permanently prescribed positions and directions by slightably adjusting the bearing 36 in the swash plate 31. The friction between the bearing 36 and the swash plate 31 holds the bearing 36, and thus the radiation emitter 2, at whatever angle at which the bearing 36 is set. As in the previous embodiments wherein the angle α can be freely selected, this only means that the angle α can be changed, as needed, from examination-to-examination, but for producing a given series of exposures for generating a tomogram, the angle α will be set at the beginning of the exposure sequence, and will be automatically and always retained at each exposure position, as the swash plate 31 is rotated by the drive 34. A predetermined connection between the radiation emitter 2, the subject to be examined and the radiation converter 16 can also be produced for preparing an x-ray exposure.

The column 3 on which the device 1, the radiation emitter 2 and the seat 7 are mounted can be a part of a movable (mobile) or a stationary stand. It is also possible to mount the device 1 and/or the radiation emitter 2 and/or the seat 7 at such a stand and/or at the wall of an examination room.

A digital, intraoral x-ray camera, for example a CCD converter, having a phosphor layer can be used as the radiation converter 16 and a conventional x-ray source for intraoral radiography that is suitable for digital exposures can be used as the radiation emitter. The x-ray source can be operated to produce a dose that can be set lower by an order of magnitude than is standard for individual digital exposures. The tomosynthetic multiple exposures thus do not require a significantly higher overall dose than is required for a single "normal" exposure.

Although modifications and changes may be suggested by those skilled in the art, it is the intention of the inventor to embody within the patent warranted hereon all changes and modifications as reasonably and properly come within the scope of his contribution to the art.

We claim as our invention:

1. An x-ray tomosynthesis installation for use in producing an image of a focal plane of a subject, comprising:

a penetrating radiation emitter which emits a beam of penetrating radiation including a reference ray;

means for coupling said radiation emitter at a plurality of different positions along a circular arc, said circular arc having a nter on said reference axis for always and automatically positioning said radiation emitter so that said reference ray intersects a reference axis perpendicular to said focal plane, at a non-zero acute angle; and means for defining said reference axis so as to be stationary with respect to said means for positioning.

2. An x-ray tomosynthesis installation as claimed in claim 1 wherein said positioning means further comprises means for setting said acute angle to a selected angular value.

3. An x-ray tomosynthesis installation as claimed in claim 1 further comprising a radiation receiver, and means for defining a distance between said means for positioning and said radiation receiver.

4. An x-ray tomosynthesis installation as claimed in claim 1 further comprising a stand, and means for mounting at least one of said radiation emitter and said means for positioning on said stand.

5. An x-ray tomosynthesis installation as claimed in claim 4 further comprising a seat for a subject to be examined using said radiation emitter, and means for pivotably mounting said seat to said stand.

6. An x-ray tomosynthesis installation as claimed in claim 4 further comprising means for movably supporting said stand.

7. An x-ray tomosynthesis installation as claimed in claim 1 further comprising means for positioning an examination subject for a dental examination using said radiation emitter.

8. An x-ray tomosynthesis installation comprising:

a radiation emitter which emits a beam of penetrating radiation including a reference ray;

means coupled to said radiation emitter for rotating said radiation emitter around a reference axis to irradiate an examination subject with said penetrating radiation from a plurality of different annular positions and for always and automatically maintaining said radiation emitter at each annular position so that said reference ray intersects said reference axis at the same acute angle; and means for defining said reference axis stationary with respect to said means for positioning.

9. An x-ray tomosynthesis installation for use in producing an image of a focal plane of a subject, comprising:

a penetrating radiation emitter which emits a beam of penetrating radiation including a reference ray;

means, including a disk coupled to said radiation emitter, for always and automatically positioning said radiation emitter so that said reference ray intersects a reference axis, perpendicular to said focal plane, at a non-zero acute angle, said disk having a recess therein for accepting said radiation emitter and a center through which said reference axis extends, and said means for positioning including means for mounting said disk for rotation around said center and said reference axis.

10. An x-ray tomosynthesis installation as claimed in claim 9 further comprising drive means for rotating said disk around said center and said reference axis.

11. An x-ray tomosynthesis installation as claimed in claim 9 further comprising a housing containing said radiation emitter and said means for positioning.

12. An x-ray tomosynthesis installation as claimed in claim 9 wherein said radiation emitter has a projecting tube through which said penetrating radiation is emitted, and wherein said disk has a recess for accepting said projecting tube.

13. An x-ray tomosynthesis installation for use in producing an image of a focal plane of a subject, comprising:

a penetrating radiation emitter which emits a beam of penetrating radiation including a reference ray;

means, including a disk coupled to said radiation emitter, for always and automatically positioning said radiation emitter so that said reference ray intersects a reference axis, perpendicular to said focal plane, at a non-zero acute angle, said disk having at least two recesses for respectively accepting said radiation emitter, said reference ray intersecting said reference axis from a first direction when said radiation emitter is accepted in one of said recesses and said reference ray intersecting said reference axis from a second, different direction when said radiation emitter is accepted in the other of said recesses; and means for defining said reference axis so as to be stationary with respect to said means for positioning.

14. An x-ray tomosynthesis installation as claimed in claim 13 wherein said means for positioning comprises an annular disk having an inside edge, and wherein said recesses respectively comprise circular segments disposed at said inside edge.

15. An x-ray tomosynthesis installation as claimed in claim 13 wherein said means for positioning comprises an annular disk having an outside edge, and wherein said recesses respectively comprise circular segments at said outside edge.

16. An x-ray tomosynthesis installation for use in producing an image of a focal plane of a subject, comprising:

a penetrating radiation emitter which emits a beam of penetrating radiation from a focus;

means for coupling said radiation emitter at a plurality of different positions along a circular arc, said circular arc having a nter on said reference axis for always and automatically positioning said radiation emitter so that said reference ray intersects a reference axis perpendicular to said focal plane, at a non-zero acute angle;

means for defining said reference axis so as to be stationary with respect to said means for positioning;

radiation receiver means for detecting radiation emitted by said radiation emitter after penetrating an examination subject, and bracket means for mounting said radiation receiver means at predetermined distance from said examination subject, from said means for positioning, and from said focus.

17. An x-ray tomosynthesis installation as claimed in claim 16 wherein said radiation receiver means has a middle region, and wherein said bracket means comprises means for mounting said radiation receiver means a distance from said focus for causing said reference ray to be incident on said middle region of said radiation receiver means and for disposing said radiation receiver means at a point on said reference axis intersected by said reference ray.

18. An x-ray tomosynthesis installation as claimed in claim 17 further comprising means for positioning an examination subject for a dental examination using said radiation emitter.

* * * * *